US008893784B2

(12) United States Patent
Abad

(10) Patent No.: US 8,893,784 B2
(45) Date of Patent: Nov. 25, 2014

(54) TRACED CHEMICALS AND METHOD TO VERIFY AND CONTROL FORMULATION COMPOSITION

(75) Inventor: Carlos Abad, Richmond, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 361 days.

(21) Appl. No.: 12/826,840

(22) Filed: Jun. 30, 2010

(65) Prior Publication Data

US 2012/0004776 A1     Jan. 5, 2012

(51) Int. Cl.
| | |
|---|---|
| *E21B 47/00* | (2012.01) |
| *G05D 11/13* | (2006.01) |
| *E21B 43/26* | (2006.01) |
| *E21B 47/10* | (2012.01) |
| *C09K 8/03* | (2006.01) |
| *G01N 21/64* | (2006.01) |
| *G01N 30/88* | (2006.01) |

(52) U.S. Cl.
CPC ...... *G05D 11/138* (2013.01); *G01N 2021/6439* (2013.01); *E21B 43/26* (2013.01); *E21B 47/1015* (2013.01); *G01N 2030/8854* (2013.01); *C09K 8/03* (2013.01)
USPC .............. 166/250.12; 166/252.6; 166/250.01

(58) Field of Classification Search
USPC ...................................... 166/250.12, 250.14
See application file for complete search history.

(56) References Cited

U.S. PATENT DOCUMENTS

| | | | | |
|---|---|---|---|---|
| 3,590,923 A | * | 7/1971 | Cooke, Jr. ................... | 166/252.6 |
| 3,623,842 A | | 11/1971 | Deans | |
| 4,722,394 A | * | 2/1988 | Wellington et al. ....... | 166/250.12 |
| 4,966,711 A | | 10/1990 | Hoots et al. | |
| 5,905,036 A | * | 5/1999 | Pope et al. ................... | 435/262 |
| 6,645,769 B2 | * | 11/2003 | Tayebi et al. .................. | 436/56 |
| 7,448,255 B2 | | 11/2008 | Hoots et al. | |
| 2004/0094297 A1 | * | 5/2004 | Malone et al. ........... | 166/250.12 |
| 2008/0236836 A1 | * | 10/2008 | Weng ............................ | 166/336 |
| 2010/0224365 A1 | | 9/2010 | Abad | |

OTHER PUBLICATIONS

SPE3792—Single-Well Tracer Method to Measure Residual Oil Saturation—Tomich, J.F., Dalton, Jr., R.L., Deans, H.A., Shallenberger, L.K. Presented at SPE Symposium on Improved Oil Recovery held in Tulsa, Oklahoma, Apr. 16-19, 1972. (1973) American Institute of Mining, Metallurgical, and Petroleum Engineers, Inc.

(Continued)

*Primary Examiner* — Zakiya W Bates
*Assistant Examiner* — Silvana Runyan
(74) *Attorney, Agent, or Firm* — Jeremy D. Tillman; Rachel E. Greene; Tim Curington

(57) ABSTRACT

Methods and apparatus to control the additives to a chemical composition for use in the oil field services industry. Specifically, a method and apparatus to determine fluid parameters for a fluid, including introducing an inert tracer in a component; forming a fluid comprising the component; observing the concentration of the tracer in the fluid; calculating the concentration of the component in the fluid; and introducing the fluid into a subterranean formation. An apparatus and method to control fluid parameters of interest for an oilfield formulation fluid such as chemical composition including introducing an inert tracer in a component; forming a fluid comprising the component; observing the concentration of the tracer in the fluid; calculating the concentration of the component in the fluid; adjusting a flow rate when forming the fluid in response to the calculating; and introducing the fluid into a subterranean formation.

21 Claims, 7 Drawing Sheets

(56) References Cited

OTHER PUBLICATIONS

SPE4104—Oil Recovery by Surface Film Drainage In Mixed-Wettability Rocks—Salathiel, R.A. Presented at the SPE-AIME 47th Annual Fall Meeting, held in San Antonio, Texas, Oct. 8-11, 1972. (1973) American Institute of Mining, Metallurgical, and Petroleum Engineers, Inc.

SPE4755—Single-Well Chemical Tracer Method to Measure Connate Water Saturation—Deans, H.A. and Shallenberger, L.K. Prepared for the Improved Oil Recovery Symposium of the Society of Petroleum Engineers of AIME, to be held in Tulsa, Oklahoma, Apr. 22-24, 1974. (1974) American Institute of Mining, Metallurgical and Petroleum Engineers, Inc.

SPE4869—A Review of Tertiary Recovery in Illinois—Lawry, T.F. Prepared for the Second Midwest Oil and Gas Industry Symposium of the Society of Petroleum Engineers of AIME, to be held in Indianapolis, Indiana, Mar. 27-29, 1974. (1974) American Institute of Mining, Metallurgical, and Petroleum Engineers, Inc.

SPE5840—Description of Field Tests to Determine Residual Oil Saturation by Single-Well Tracer Method—Sheely, C.Q. Presented at the SPE-AIME Improved Oil Recovery Symposium, held in Tulsa, Mar. 22-24, 1976, (1978) Society of Petroleum Engineers of AIME.

SPE6047—In-Situ Determination of Residual Gas Saturation by Injection and Production of Brine—Bragg, J.R., Shallenberger and Deans, H.A. Prepared for the 51st Annual Fall Technical Conference and Exhibition of the Society of Petroleum Engineers of AIME, held in New Orleans, Oct. 3-6, 1976. (1976) American Institute of Mining, Metallurgical, and Petroleum Engineers, Inc.

SPE6370—Oil Saturation Measurements at Brown and East Voss Tannehill Fields—O'Brien, L.J., Cooke, R.S. and Willis, H.R. Presented at the SPE-AIME Permian Basin Oil and Gas Recovery Conference, held in Midland, Texas, Mar. 10-11, 1977. (1978) Society of Petroleum Engineers of AIME.

SPE/DOE14886—Single-Well Tracer Test in Complex Pore Systems—Deans, H.A. and Carlisle, C.T. Prepared for presentation at the SPE/DOE Fifth Symposium on Enhanced Oil Recovery of the Society of Petroleum Engineers and the Department of Energy held in Tulsa, Oklahoma, Apr. 20-23, 1986. (1986) Society of Petroleum Engineers.

SPE14887—Evaluation and Comparison of Residual Oil Saturation Determination Techniques—First presented at the 1986 Enhanced Oil Recovery Symposium held in Tulsa, Apr. 20-23. SPE Formation Evaluation, Mar. 1988. pp. 251-262.

SPE/DOE24136—A Single-Well Tracer Test to Estimate Wettability—Ferreira, L.E.A., Descant, F.J., Delshad, M., Pope, G.A.,and Sepehrnoori, K. Prepared for presentation at the SPE/DOE Eighth Symposium on Enhanced Oil Recovery held in Tulsa, Oklahoma, Apr. 22-24, 1992. (1992) Society of Petroleum Engineers Inc.

SPE28591—Chemical Tracer Studies to Determine Water Saturation at Prudhoe Bay—Deans, H.A. and Mut, A.D First presented at the 1994 SPE Annual Technical Conference and Exhibition, New Orleans, Sep. 25-28, (1997) Society of Petroleum Engineers.

SPE48951—Design, Implementation and Simulation Analysis of a Single-well Chemical Tracer test to Measure the Residual Oil Saturation to a Hydrocarbon Miscible Gas at Prudhoe Bay—Cockin, A.P., Malcolm, L.T., McGuire, P.L., Giordano, R.M., Sitz, C.D. Prepared for presentation at the 1998 SPE Annual Technical Conference and Exhibition held in New Orleans, Louisiana, Sep. 27-30, 1998. (1998) Society of Petroleum Engineers, Inc.

SPE68051—Analysis of a Single-Well Chemical Tracer Test to Measure the Residual Oil Saturation to a Hydrocarbon Miscible Gas Flood at Prudhoe Bay—Cockin, A.P., Malcolm, L.T., McGuire, P.L., Giordano, R.M., Sitz, C.D. Revised for publication from paper (SPE 48951, prepared for presentation at the 1998 SPE Annual Technical Conference and Exhibition, New Orleans, Sep. 27-30. (2000) Society of Petroleum Engineers.

SPE75122—Single Well Chemical Tracer Test to Determine ASP Injection Efficiency at Lagomar VLA-6/9/21 Area, C4 Member, Lake Maracaibo, Venezuela—Hernandez, C., Chacon, L., Anselmi, L., Angulo, R., Manrique, E., Romero, E., De Audemard, N. and Carlisle, C. Prepared for presentation at the SPE/DOE Improved Oil Recovery Symposium held in Tulsa, Oklahoma, 13-17, 2002. (2002) Society of Petroleum Engineers, Inc.

SPE93903—Low Salinity Oil Recovery: An Exciting New EOR Opportunity for Alaska's North Slope—McGuire, P.L., Chatham, J.R., Paskvan, F.K., Sommer, D.M., Carini, F.H. Prepared for presentation at the 2005 SPE Western Regional Meeting held in Irvine, California, USA, Mar. 30-Apr. 1, 2005. (2005) Society of Petroleum Engineers Inc.

SPE102239—Modeling Low-Salinity Waterflooding—Jerauld, G.R., Lin, C.Y., Webb, K.J., and Seccombe, J.C. Prepared for presentation at the 2005 SPE Annual Technical Conference and Exhibition held in San Antonio, Texas USA Sep. 24-27, 2006. (2006) Society of Petroleum Engineers.

The Single-Well Chemical Tracer Test—A Method for Measuring Reservoir Fluid Saturations in Situ—Deans, H. and Carlisle, C. Petroleum Engineering Handbook—Larry W. Lake Editor-in-chief. vol. 5, Reservoir Engineering and Petrophysics—Edward D. Holstein, Editor. Chapter 5, pp. V615-V649. (2007) Society of Petroleum Engineers.

* cited by examiner

TRACED CHEMICALS AND METHOD TO VERIFY AND CONTROL FORMULATION COMPOSITION

BACKGROUND

1. Field of the Invention

Embodiments of this invention relate to oil field services operations. Specifically, embodiments of this invention relate to ways to control additives to a hydraulic fracturing operation.

2. Description of the Related Art

Hydraulic fracturing is a process for stimulating oil and gas wells by pumping gel-sand slurries at high pressure into producing rock layers. Once the rock is cracked, the resulting fracture is propped open by the sand carried by the slurry. This fracture serves as a highly conductive path for the oil or gas, and therefore increases the effective well-bore radius. Fluid viscosity is vital for effective proppant placement during fracturing operations. Polysaccharides such as guar and guar derivatives have historically served as the most common viscosity enhancers. They are often crosslinked using borates or metallic crosslinkers such as zirconium and titanium to generate even higher viscosity. Multiple additives are added to each formulation. Pre-job Quality Assurance/Quality Control (QA/QC) is performed on location minutes before beginning to pump to ensure the fluid performs as required.

A major challenge in hydraulic fracturing operations is how to ensure that the fluid that is being pumped continuously is an exact match to the performance it was designed for. Fluid formulations during the treatment are controlled by maintaining given additive concentrations in control through close loop control strategies managed with pumps and flowmeters, for which one point calibration verification is carried out through a pre-job "bucket check". No redundancy is typically incorporated. Samples of the fluid are manually taken at significant events, (begin of pumping, begin of proppant pumping, change of proppant concentration) but this can only be done sparsely. Typically, visual inspection of the fluid's ability to transport proppant is carried out.

Also, cementing is a process for zonal isolation. In this process, multiple additives, retarders, accelerators, dispersants, foamers are added to the mix water prior to the addition of the cement slurry. Controlling the exact concentration of each of the additives either on the fly or when water is batch mixed is key for the successful execution of the treatment.

Gravel pack, fracturing and packing, matrix acidizing, wellbore clean out, wellbore remediation, conformance control, additive squeeze treatments such as organic and inorganic scale removal treatments, hydrate or asphaltene prevention treatments, well abandonment pills, filter cake removal treatments, and others are all well service operations that require some level of chemical formulation mixing and preparation, and for which the ability to formulate the fluid as per design is very important for the treatment effectiveness, and eventually to be able to respond in real time to predesigned formulation changes, or unforeseen changes required as a result of the reception and or evaluation of stimuli and responses from the formation, the reservoir, or the downhole completion.

For example, FIG. 1 describes the common control of chemical composition in well service treatments when an open loop strategy is used as a method for fluid delivery control. In the figure, a chemical A (110), in a fluid form, such as to deliver a concentration of chemical per unit volume $C_A^0$, is pumped through a metering pump (120) at a flow rate FA. The flow rate is typically set by a frequency, voltage, or current proportional to the pumping rate of the pump, as typically determined by calibration, and in multiple occasions might be verified by a mass flowmeter (130). Frequently the calibration is set by the pump manufacturer, given a certain set of physical parameters in the pump (range, size of stroke, etc), and verified prior to the job execution by a volumetric determination of fluid delivered in a pre-set amount of time, what is commonly called a "bucket check." The actual concentration of chemical A delivered through stream FT (140), into the well, CA (150) can be calculated as $CA = C_A^0 * FA/(FA+FT)$.

FIG. 2 further describes potential sources of error in the concentration of chemical as delivered for the treatment as a result of using the control strategy described above. A "bucket check" shown as point (210) and error (220) resulted in a deviation (230) of the assigned set point to the flow $FA^{SP}$ (240) from the desired set point $FA^{SP}$real (250). In addition, the conditions during the trip caused the delivered flow rate FA (260) to drift from the original set point by an additional error (270). From the calculation of the concentration delivered into the well CA in FIG. 1, it is clear that any error in delivering the exact flow rate FA would subsequently result in an error on the delivered concentration. From these examples, it is demonstrated that open loop control strategies can be a source of error when attempting to deliver accurate concentrations of chemicals during well service treatments.

FIG. 3 shows a modified state with respect to control of chemical composition in well service treatments when a closed loop strategy is used as a method for fluid delivery control. In the figure, a chemical A (310), sourced from a chemical manufacturer in a fluid form, such as to deliver a concentration of chemical per unit volume $C_A^0$, is pumped through a metering pump (320) at a flow rate FA. The flow rate is typically set by a frequency, voltage, or current proportional to the pumping rate of the pump, as typically determined by calibration, and in multiple occasions might be verified by a mass flowmeter (330). Frequently the calibration is set by the pump manufacturer, given a certain set of physical parameters in the pump (range, size of stroke, etc), and verified prior to the job execution by a volumetric determination of fluid delivered in a pre-set amount of time, what is commonly called a "bucket check." In addition, and electronic feed-back control loop (340) is established comparing the required set point as per the bucket calibration $FA^{SP}$ (350) to the actual measurement as determined by the flow meter FA (360), and modifying the input signal to the pump w (370) according to known control algorithm, typically a PID (proportional Integral Derivative) controller based on the measured difference between both set point and actual value. The actual concentration of chemical A delivered through stream FT (380), into the well CA (390) can be calculated as $CA = C_A^0 * FA/(FA+FT)$. Typically PID controllers are very effective to maintain the desired set-point, and thus the actual delivered concentration can be assumed to be close to the averaged value $CA = C_A^0 * FA^{SP}/(FA^{SP}+FT)$.

FIG. 4 further describes a potential source of error in the concentration of chemical a delivered for the treatment as a result of using the control strategy described above for FIG. 3. A "bucket check" shown as point (410) and error (420) resulted in a deviation (430) of the assigned set point to the flow $FA^{SP}$ (440) from the desired set point $FA^{SP}$real (450). In addition, the conditions during the trip caused the delivered flow rate FA (460) to drift from the original set point by an additional error (470). This error is minimized by the feedback loop controller as compared to that of FIG. 2, as a result of the signal delivered to the pump w (480) varying as a response to the treatment conditions causing a drift in the flow delivered by the pump at constant rate as per FIG. 2. From the calculation of the concentration delivered into the well CA in FIG. 3, it is clear that any error in delivering the exact flow rate FA would subsequently result in an offset error on the delivered concentration. From FIGS. 3 and 4 it is demonstrated that closed loop control strategies, while typically more reliable than open loop strategies at maintaining a constant output, can also be a source of error when attempting to deliver accurate concentrations of chemicals during well service treatments, due to the offset error intrinsic to the "bucket check." Those skilled in the art will select the appropriate control strategy given the equipment available on location, and the required flow rates to be deliver. Since the equipment deployed is to be used for treatments involving high pumping rates as well as low pumping rates, it often occurs that the target flow rates are not necessarily fitting in the optimum range for delivery by the field equipment. In some cases, it is necessary to resort to dilution of the chemicals in location in order to minimize the pumping associated errors.

FIG. 5 further shows potential sources of error in the concentration of chemical A as delivered for a treatment as a result of the variability associated with manufacturing, handling and dilution of the chemical. The chemical plant manufacturing aims to obtain a constant chemical concentration $C_A^0$ (510) but in reality a distribution of chemical compositions (520) within the lower (530) and upper (540) control limits $C_A^{LSL}$ $C_A^{USL}$ respectively, is obtained. Additional variability is obtained when such distribution is diluted three times aiming to obtain a target concentration $\frac{1}{3} C_A^0$ (550) producing in return a new distribution of concentrations (560).

To summarize, a method for estimating and/or confirming a fracturing fluid composition as the fluid is formed, before it is introduced to the wellbore that is effective, quick, and economical is needed.

SUMMARY

Embodiments of this invention relate to methods and apparatus to control the additives to a chemical composition for use in the oil field services industry. Specifically, embodiments relate to a method and apparatus to determine fluid parameters for a fluid, including introducing an inert tracer in a component; forming a fluid comprising the component; observing the concentration of the tracer in the fluid; calculating the concentration of the component in the fluid; and introducing the fluid into a subterranean formation. Embodiments of the invention relate to an apparatus and method to control fluid parameters of interest for an oilfield formulation fluid such as chemical composition including introducing an inert tracer in a component; forming a fluid comprising the component; observing the concentration of the tracer in the fluid; calculating the concentration of the component in the fluid; adjusting a flow rate when forming the fluid in response to the calculating; and introducing the fluid into a subterranean formation.

DETAILED DESCRIPTION

Figure 1:
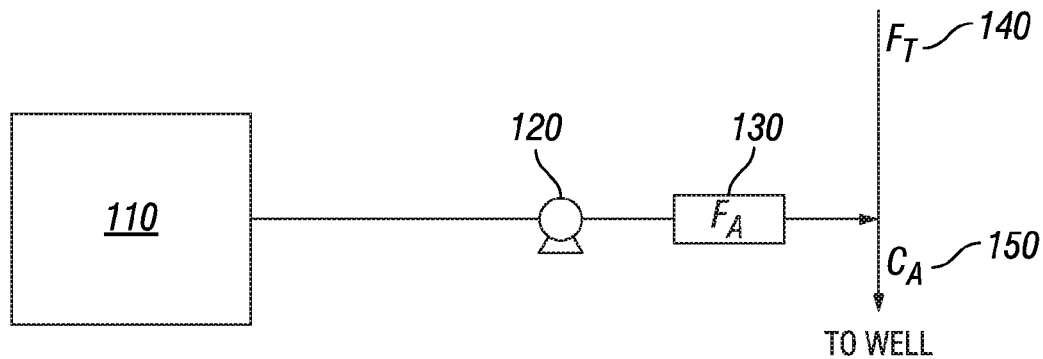
FIG. 1 (prior art) illustrates an open loop strategy for fluid delivery control.
Figure 2:
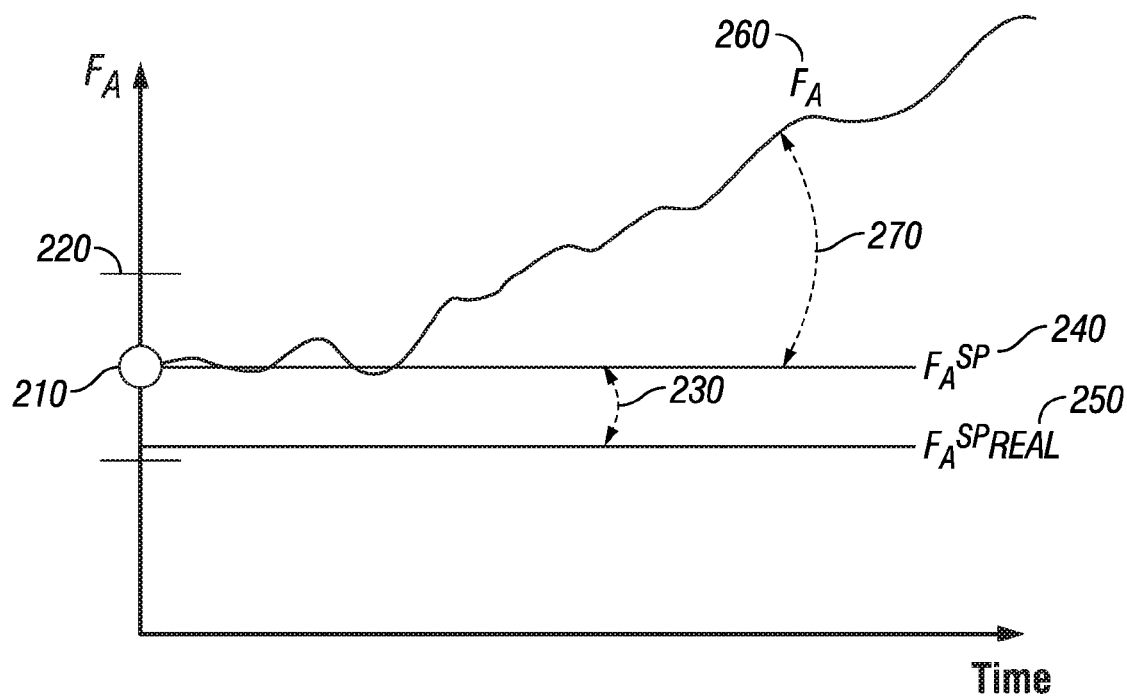
FIG. 2 (prior art) is a representation of error in the concentration of chemical as delivered in an embodiment such as that illustrated by FIG. 1.

At the outset, it should be noted that in the development of any such actual embodiment, numerous implementation—specific decisions must be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary of the invention and this detailed description, each numerical value should be read once as modified by the term "about" (unless already expressly so modified), and then read again as not so modified unless otherwise indicated in context. Also, in the summary of the invention and this detailed description, it should be understood that a concentration range listed or described as being useful, suitable, or the like, is intended that any and every concentration within the range, including the end points, is to be considered as having been stated. For example, "a range of from 1 to 10" is to be read as indicating each and every possible number along the continuum between about 1 and about 10. Thus, even if specific data points within the range, or even no data points within the range, are explicitly identified or refer to only a few specific, it is to be understood that inventors appreciate and understand that any and all data points within the range are to be considered to have been specified, and that inventors possessed knowledge of the entire range and all points within the range.

The statements made herein merely provide information related to the present disclosure and may not constitute prior art, and may describe some embodiments illustrating the invention.

Methods of analysis of chemical composition following online mixing, or after batch mixing becomes troublesome, and a final mass balance is the best we can do to provide the customer with a measurement of what has been pumped downhole. Disclosed is a method useful to monitor composition of formulations after the whole mix has been prepared, by measuring the concentration of strong signaling tracers in the final fluid formulation, with known analytical methods, provided that said tracers are included in known concentrations in the pumped chemicals as sourced. Different tracers with distinct signals are required for each chemical participating in the formulation. Methods of signal deconvolution, principal component analysis, inversion, and the like might be needed for analysis of the signal from the formulation in order to provide an accurate measurement of the composition. The method can be used for monitoring the concentration one, various or all the components in the formulation.

A method for the verification of the accuracy of a chemical formulation using chemical tracers is provided. The chemical composition could be a formulation partially prepared at a chemical plant, a formulator, a mixer, a district lab, or a well servicing site. The formulation might be prepared as a batch, semibatch or continuous operation, and may include multiple formulating stages, and measurement points, and could be used for batch mixing or on-the fly mixing of additives.

Figure 6:
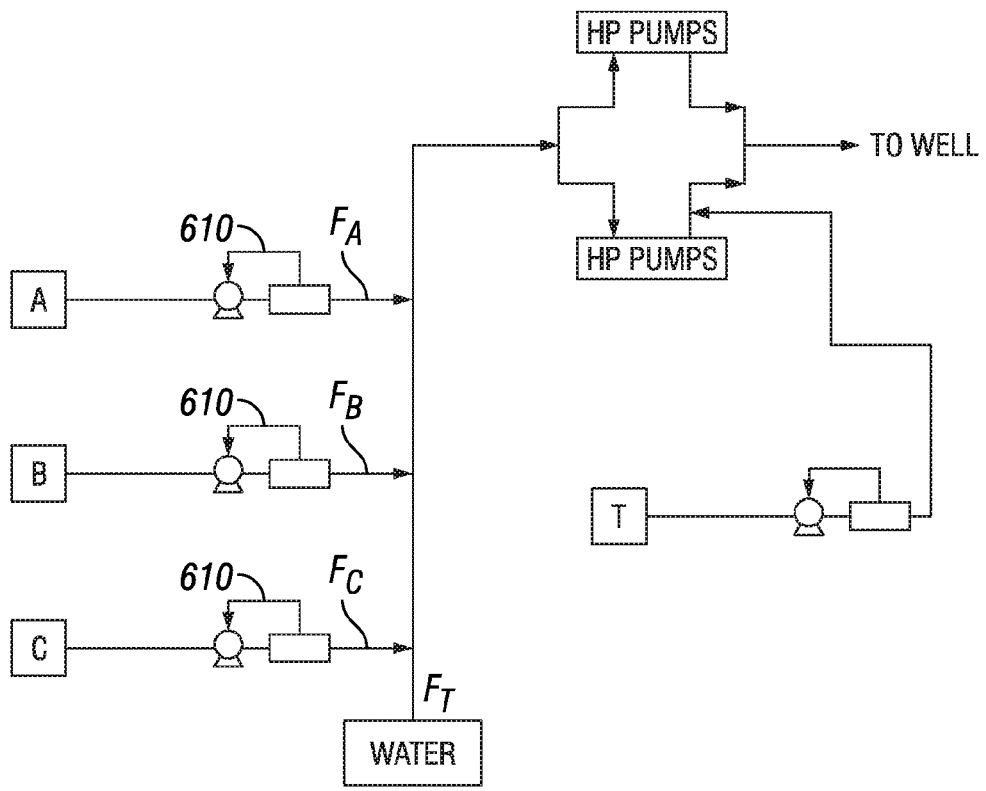
FIG. 6 (prior art) illustrates a control scheme using a tracer to trace fluid flow in a wellbore and/or subterranean formation.

Tracers are commonly employed in well servicing treatments as a mean to determine flow distribution patterns of the fluids as they are exposed to the wellbore and/or subterranean formation. Such measurements are provided by injecting a tracer into a fluid injected in one well and measuring its concentrations in neighboring wells or by injecting different tracers in various stages of a treatment, for instance a multi-stage fracturing treatment in order to determine if crossflow across various fractures is obtained, or to determine preferential production. FIG. 6 (prior art) shows a typical treatment where various chemical additives A, B and C (610) are pumped as per FIG. 3, while a tracer T (620) is pumped with a similar control loop (630) into the high pressure zone of a fracturing treatment (640).

In one embodiment of the invention, a method to determine fluid parameters of interest for an oilfield formulation fluid such as chemical composition at surface is provided. The method is based in introducing a series of different inert tracers of known concentration selected components of the mixture, which can be detected independently by different measurement methods, performing said measurements on the formulated fluid, calculating and reporting the concentration of each of the tracers in the formulation, back calculating the concentration of each of the components in the formulation. The term inert tracer is used to indicate that the tracer is added in a concentration that is low enough not to contribute to the performance of the oilfield formulation.

The tracer is incorporated prior to the delivery of the chemical compound to the location, typically by the manufacturer. Different tracers are incorporated to different chemicals whose concentration in the ultimate fluid composition is to be estimated. It is possible that all chemicals delivered as separate streams to the formulation either continuously, or in batch mode include at least one tracer. It is possible that some of the chemicals in the formulation do not include any tracer. It is possible that some chemicals include more than one tracer. Both chemical and tracer can be delivered in the field in any shape or form, including liquid, solid, gas, solution, dispersion, and the like. A tracer can be a particular atom, ion, complex, molecule, polymer, group of molecules with a particular characteristic that makes them easily distinguishable from the rest of the chemicals in the formulation.

Tracers that can be incorporated into the various chemicals are organic molecules that can be detected by methods such as liquid or gas chromatography. Examples of such chemicals are linear or branched hydrocarbons, saturated or aromatic hydrocarbons, polycyclic hydrocarbons, waxes, resins, and the like. Such chemical compounds contain carbon and hydrogen atoms that can be detected by gas chromatography detectors such as TCD, ECD or FID, chemical compounds containing heteroatoms such as nitrogen, can also be used as tracers, and be detected with sulfur and nitrogen sensitive chromatography detectors. Alternatively total carbon concentration can also be used following flash evaporation of the fluid. Organic molecules containing chromophore groups (absorbing, fluorescing, or phosphorescing in the visible or UV region of the light spectrum, such as those tracers comprising a UV-VIS chromophore) can also be used as tracers. Dyes are examples of effective tracers, for which one or multiple wavelengths can be used to detect the tracer concentration. Ions in solution or metal atoms in dispersion of various nuclei of varying properties such as charge, isotope mass, or even radioactivity, are also effective tracers that can be detected with analytical methods such as ion selective sensors, gamma ray emission detectors, ICP, and the like. When selecting the tracers it is preferable to select various tracer that can be detected and quantified with the same technique even if it is by multiple channels.

In another embodiment of the invention the method to determine the fluid parameters of interest of an oilfield formulation fluid is carried out by sampling discrete aliquots of the fluid, but more preferably is carried out continuously. The method can be applied to oilfield operations carried out in batch or continuously, both in steady or in transient state In another embodiment of the invention fluid at least one of the tracers used is not an inert tracer, in other words it is a chemical which is an active component of the oilfield fluid formulation.

In another embodiment of the invention the test method used to detect the tracers is the same type of measurement with multiple detection channels. Test methods that can be used for the invention can be for instance spectroscopy such as UV absorbance, UV fluorescence, IR, FTIR, NIR, raman, or other techniques such as pH, conductivity, voltametry, voltamperometry, ion selective electrodes, and the like. Different measurement methods can be used for different tracers. Alternatively, the same detection method can be used, provided that different detection channels are used for each tracers. Different detection channels can be used, for instance multiple absorbing wavelengths for. In addition more than one detection channel might be required to detect a given tracer if substantial overlap exists between the response of various tracers for a certain channel, for instance in the case of various tracers with differentiated UV absorbance profiles.

In another embodiment, the information about the fluid parameters of interest determined by the methods disclosed herein is used to further adjust chemical composition or other similar parameters of the formulation, either in a batch process or in a continuous process.

In another embodiment, the information about the fluid parameters of interest determined by the methods disclosed herein is used to predict downhole fluid performance by means of suitable algorithms and correlations. Downhole fluid performances of interest are those such as viscosity, degree of crosslinking, rate of crosslinking, etc. Some details of how the downhole fluid performs are provided in United States Patent Application Publication No. 2010/00224365, which is hereby incorporated by reference in its entirety.

In another embodiment, the information about the fluid parameters of interest determined by the methods disclosed herein is used in combination with other unrelated measurements such as pressure, density, rate, temperature and others to understand formation, reservoir, or downhole completion response to the treatment, such as fracture propagation, formation permeability, fluid diversion, flow path reduction and screen-out, valve positioning, etc. Some additional details of how the downhole fluid performs are provided in United States Patent Application Publication No. 2010/0224365.

Figure 3:
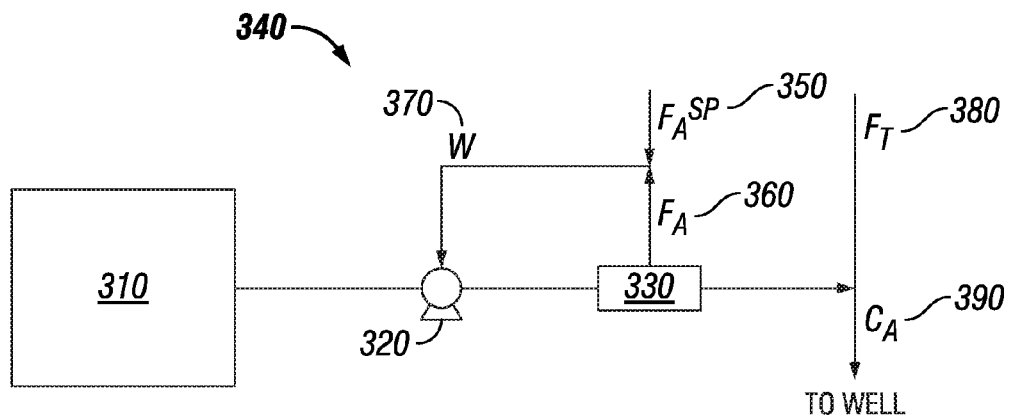
FIG. 3 (prior art) is an alternative strategy to control a chemical composition in well service treatments using a closed loop strategy for fluid delivery control.
Figure 4:
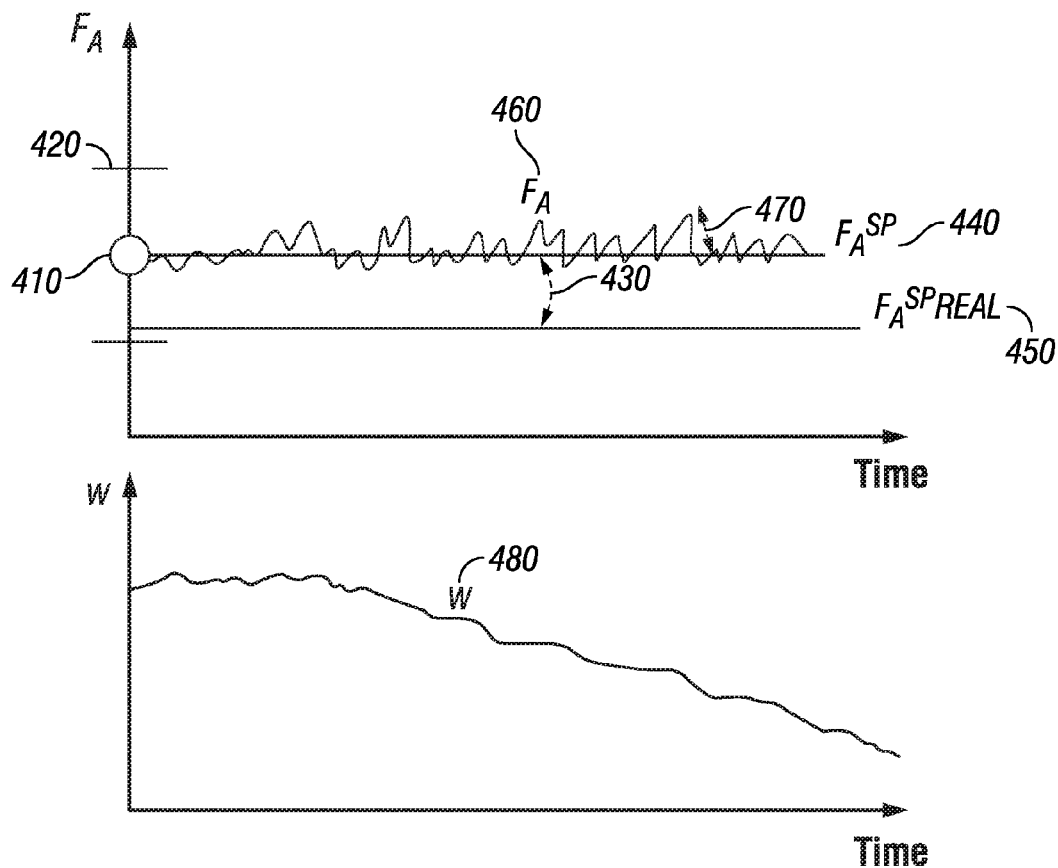
FIG. 4 (prior art) is a representation of error in the concentration of chemical as delivered in an embodiment such as that illustrated by FIG. 3.
Figure 5:
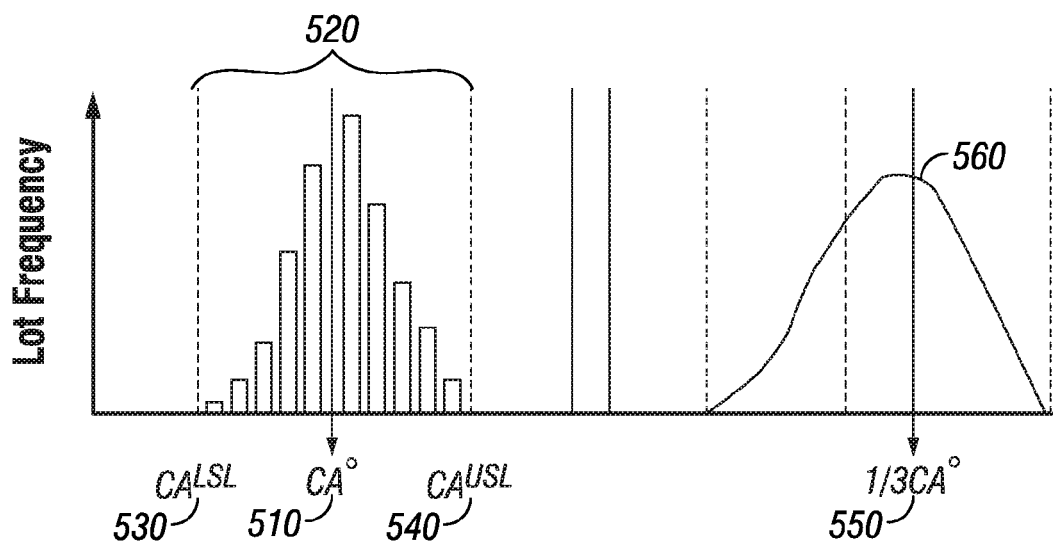
FIG. 5 (prior art) is a representation of error in the concentration of chemical A as delivered for a treatment as a result of the variability associated with manufacturing, handling and dilution of chemical A.
Figure 7:
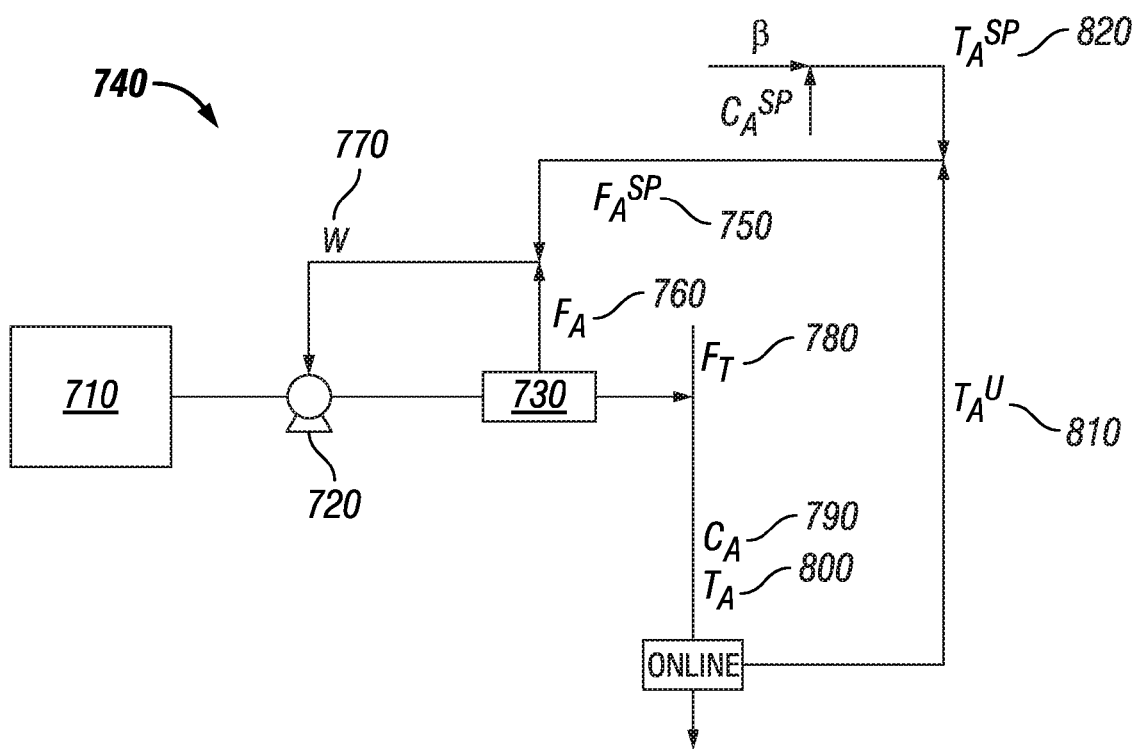
FIG. 7 provides an embodiment of a control scheme of a chemical composition in well service treatments when a cascade control loop is added to the closed loop strategy of FIG. 3 based on the measurement of tracers embedded in the composition.

FIG. 7 shows control of chemical composition in well service treatments when a cascade control loop is added to the closed loop strategy in FIG. 3 based on the measurement of tracers embedded in the formulation chemicals. In FIG. 7, a chemical A (710), sourced from a chemical manufacturer in a fluid form, such as to deliver a concentration of chemical per unit volume $C_A^0$, also including a concentration of a tracer TA $T_A^0$, is pumped through a metering pump (720) at a flow rate FA. The ratio of concentrations of tracer to chemical 13 is calculated as $\beta = T_A^0/C_A^0$. The flow rate is typically set by a frequency, voltage, or current proportional to the pumping rate of the pump, as typically determined by calibration, and in multiple occasions might be verified by a mass flowmeter (730). Frequently, the calibration is set by the pump manufacturer, given a certain set of physical parameters in the pump (range, size of stroke, etc), and verified prior to the job execution by a volumetric determination of fluid delivered in a pre-set amount of time, what is commonly called as "bucket check". In addition, and electronic feed-back control loop (740) is established comparing the required set point as per the bucket calibration $FA^{SP}$ (750) to the actual measurement as determined by the flow meter FA (760), and modifying the input signal to the pump w (770) according to known control algorithm, typically a PID (proportional Integral Derivative) controller based on the measured difference between both set point and actual value. The actual concentration of chemical A delivered through stream FT (780), into the well CA (790) can be calculated as $CA = C_A^0 \cdot FA/(FA+FT)$. The concentration of tracer delivered into the well TA (790) can be calculated as $TA = T_A^0 \cdot FA/(FA+FT)$. According to the invention, a method to determine the concentration of tracer TA in the flow stream FT is deployed online (800). The measured concentration $TA^\mu$ (810) is compared to the expected concentration $TA^{SP}$ (820), that can be determined from the target concentration of chemical A $CA^{SP}$, and the actual ratio of concentrations $\beta$ as $TA^{SP} = \beta \, CA^{SP}$. The difference is used as the master setpoint for the cascade controller, establishing by means of a typical control loop (PID, PI) a new set point for the flow rate of chemical a to be delivered $FA^{SP}$. Typically PID controllers are very effective to maintain the desired set-point, and thus the actual delivered concentration can be assumed to be close to the averaged value $CA = C_A^0 \cdot FA^{SP}/(FA^{SP}+FT)$, where in this case $FA^{SP}$ is varied according to the difference in actual tracer concentration as measured on-line.

Figure 8A:
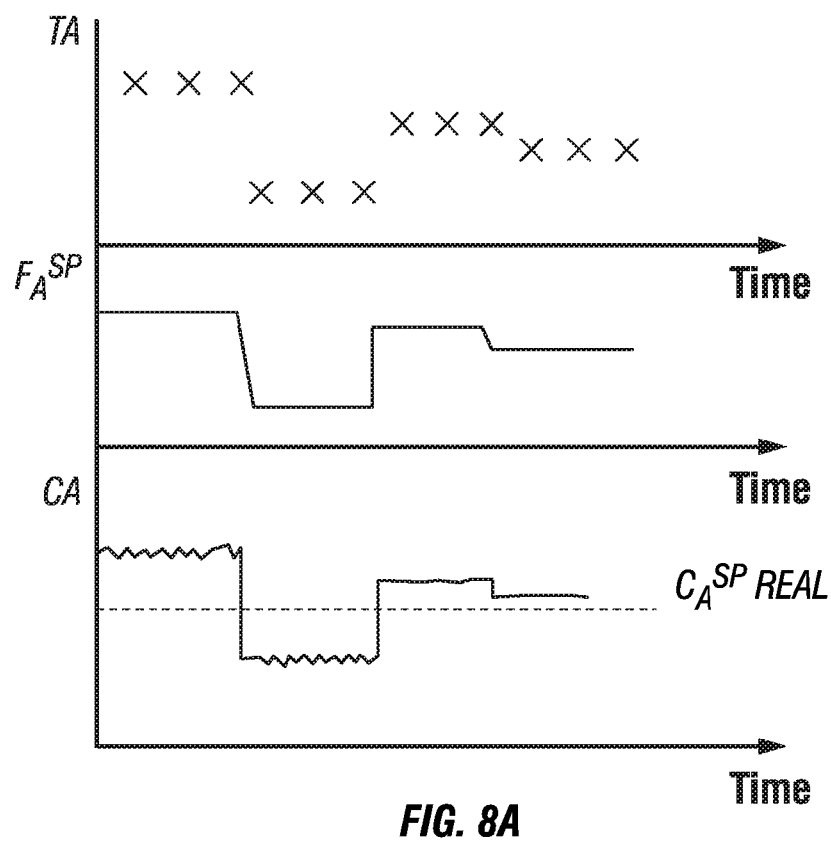
FIGS. 8A and 8B provide an embodiment of a control scheme of a chemical composition in well service treatments such as those illustrated by FIG. 7.
Figure 8B:
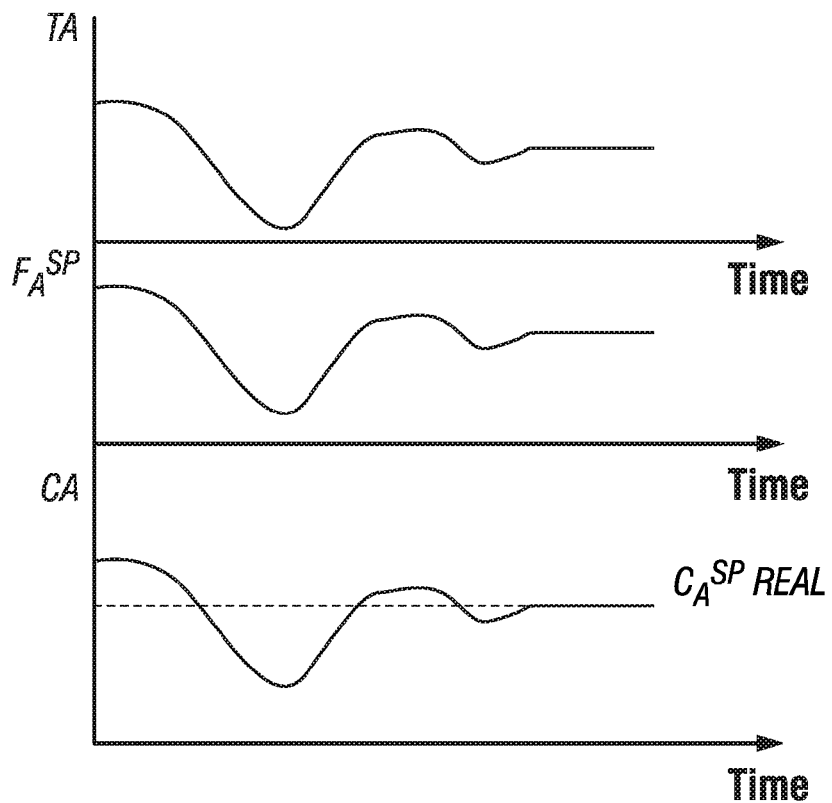

FIGS. 8A and 8B show a control of chemical composition in well service treatments as described in the discussion of FIG. 7 above. In FIG. 8A, discontinuous measurements of concentration of tracer Tam are used to determine the required set point for the flow rate of chemical A, $FA^{SP}$. As a response the actual concentration of chemical A serving as an effective control method. In FIG. 8B, continuous measurements of concentration of tracer Tam are used to determine the required set point for the flow rate of chemical A, $FA^{SP}$. As a response the actual concentration of chemical A serves as an effective control method.

Figure 9:
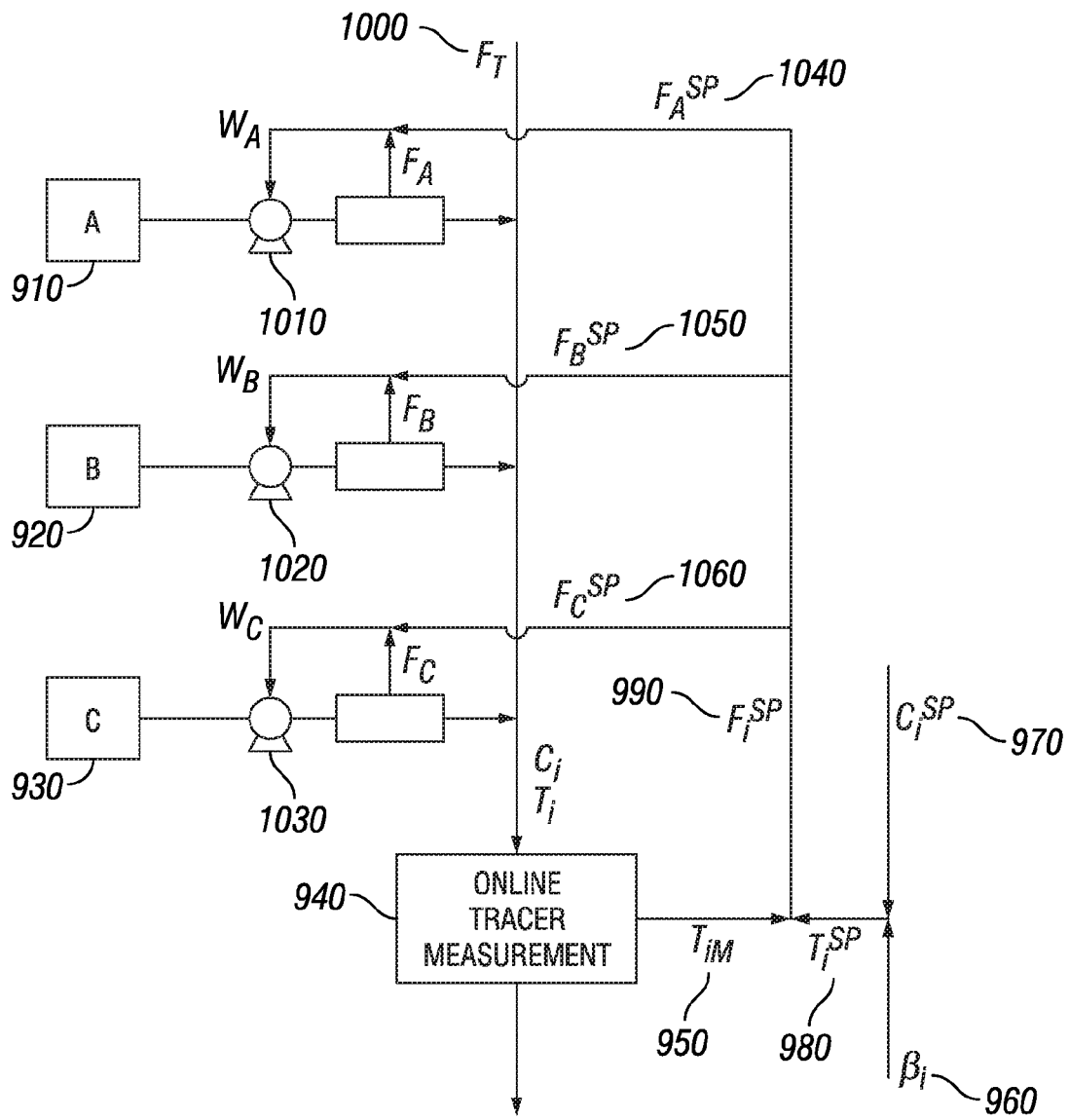
FIG. 9 provides an embodiment of a control scheme of a chemical composition in well service treatments with multiple cascade control loops.

FIG. 9 shows control of chemical composition in well service treatments when multiple cascade control loops are added to the closed loop strategy in illustrated by FIG. 3 based on the measurement of tracers embedded in the formulation chemicals. In FIG. 9, the flow of various chemicals A (910), B (920) and C (930) in a fluid form, such as to deliver respectively concentrations of chemical per unit volume $C_A^0$, $C_B^0$, and $C_C^0$, also including each a concentration of a different tracer TA, TB, and TC respectively of $T_A^0$, $T_B^0$, $T_C^0$, are controlled through a cascade loop controls (1010, 1020 and 1030) respectively at flow rates FA, FB and FC, that can be in general be described as Fi The ratio of concentrations of tracer to chemical $\beta_i$ is calculated as $\beta_i = T_i^0/C_i^0$. The actual concentration of chemical A delivered through stream FT (1000), into the well Ci can be calculated as $Ci = C_1^0 \cdot Fi/(Fi+FT)$. The concentration of tracer delivered into the well Ti can be calculated as $Ti = T_i^0 \cdot Fi/(Fi+FT)$. According to the invention, a method to determine the concentration of tracer Ti in the flow stream FT is deployed online (940). The measured concentration Tim (950) is compared to the expected concentration $Ti^{SP}$, that can be determined from the target concentration of chemical i $Ci^{SP}$ (970), and the actual ratio of concentrations $\beta_i$ (960) as $Ti^{SP} = \beta i \, Ci^{SP}$ (980). The difference is used as the master setpoint for each the cascade controller, establishing by means of a typical control loop (PID, PI) a new set point for the flow rate of chemical a to be delivered $Fi^{SP}$ (990). Typically PID controllers are very effective to maintain the desired set-point, and thus the actual delivered concentration can be assumed to be close to the averaged value $Ci = C_i^0 \cdot Fi^{SP}/(Fi^{SP}+FT)$, where in this case $FA^{SP}$ (1040), $FB^{SP}$ (1050), $FC^{SP}$ (1060), is varied according to the difference in actual tracer concentration as measured on-line.

Figure 10:
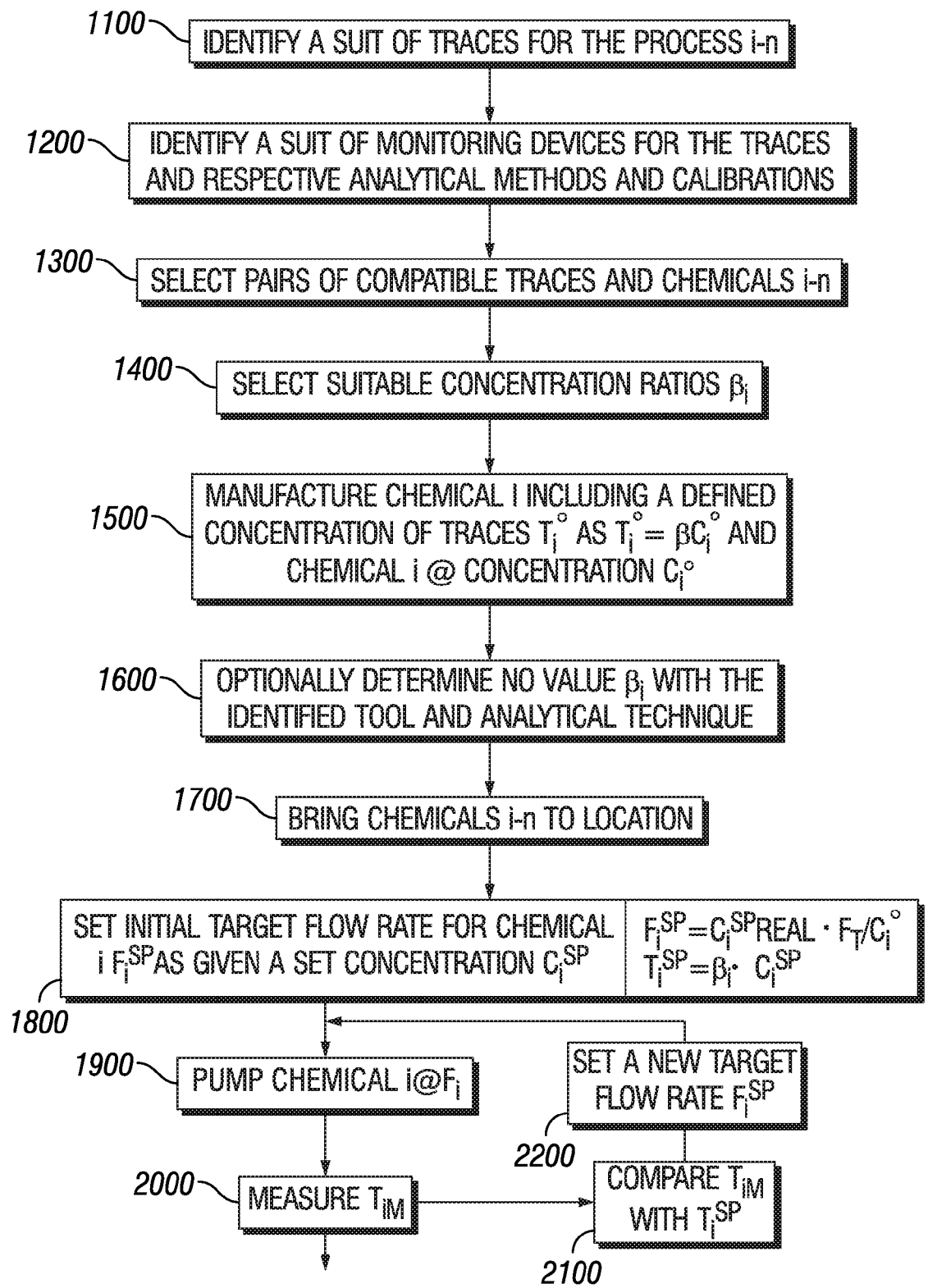
FIG. 10 is a flow chart of process steps of one embodiment of the invention.

FIG. 10 is a flow chart illustrating an embodiment that summarizes the overall process. First, a suit of tracers for the process (form i to n) are identified (1100), then a suit of monitoring devices and test methods for the tracers in the fluid, and suitable calibration curves are identified (1200); then treatment chemicals and tracers are paired according to suitable compatibility rules (1300), then suitable concentration ratios $\beta i$ are identified (1400); the chemicals are manufactured including defined concentrations of chemical $C_i^0$ and tracer $T_i^0$ such as $\beta i = T_i^0/C_i^0$ (1500); then optionally the value $\beta i$ is determined experimentally as a quality control method (1600). Then, the chemicals are brought to location (1700); initial target flow rates for the chemicals $Fi^{SP}$ are set given the required concentrations $Ci^{SP}$ (1800). The treatment is commenced by pumping chemical i at flow rate Fi (1900); the tracer i concentration is measured as Tim (2000); this value is compared to the target required tracer concentration $Ti^{SP}$ (2100), and subsequently the target flow for chemical i is modified according to the control algorithm as described above with FIG. 7 (2200). The process is continued during the duration of the treatment. In some cases the design requires the target concentration of chemical i $Ci^{SP}$ to be altered as a function of time. In these cases, the target tracer concentrations $Ti^{SP}$ can be varied accordingly and the cascade control method introduced continued with time dependent set point concentrations.

In some cases, the target $Fi^{SP}$ flow for chemical i is modified by sending and electric or electronic signal to the pump, screw feeder, shaker feeder, control valve, or the flow meter. Often times a remote PLC or controller is used to receive the new target flow $Fi^{SP}$ to ensure that the appropriate level of local control is introduced to the loop. Alternatively a control program residing on a computer can be used as the recipient of the new target $Fi^{SP}$. In some occasions the target $Fi^{SP}$ is not send to the local equipment remotely via wired or wireless communication, but is implemented manually by means of a human intervention through a human interface such as a keyboard, a display, or a dial and the like.

While most of the examples presented in this application have been referred to the flow of liquid streams, and thus the selected control elements and measurement elements are pumps and flow meters, several other methods of rate measurement control such as balances or load cells, and screw feeders or shake feeders, or pressure indicator and variable chokes or valves such as control valves can be envisioned as also pertaining to the invention. Those of skill in the art will be able to easily select those elements of control that suit best the physical characteristics and environmental conditions of the treatment for liquids, solutions, slurries, gases, solids, dispersions, emulsions and the like.

The particular embodiments disclosed above are illustrative only, as the invention may be modified and practiced in different but equivalent manners apparent to those skilled in the art having the benefit of the teachings herein. Furthermore, no limitations are intended to the details herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method to control fluid parameters for a fluid, comprising:
   introducing a tracer in a component;
   forming a fluid comprising the component that contains the tracer;
   determining a concentration of the tracer in the fluid online;
   estimating a concentration of the component in the fluid based on the online determination of the concentration of the tracer in the fluid;
   introducing the fluid into the subterranean formation at a flow rate; and
   adjusting the flow rate of the fluid into the subterranean formation based on the estimated concentration of the component in the fluid.

2. The method of claim 1, further comprising adjusting a concentration of the component based on the online determination of the concentration of the tracer in the fluid.

3. The method of claim 1, further comprising adjusting an addition rate of the component based on the online determination of the concentration of the tracer in the fluid.

4. The method of claim 3, wherein the adjusting the addition rate of the component comprises sending a signal to a pump.

5. The method of claim 3, wherein the adjusting the addition rate of the component comprises changing a flow rate of the component.

6. The method of claim 1, further comprising introducing a second tracer in a second component and wherein the fluid further comprises the second component.

7. The method of claim 1, wherein the tracer comprises organic molecules that can be quantified by liquid or gas chromatography.

8. The method of claim 1, wherein the tracer comprises organic molecules that can be detected by chromatography detectors.

9. The method of claim 1, wherein the tracer comprises organic molecules that can be detected by UV or visible spectroscopy.

10. The method of claim 1, wherein the tracer comprises at least one chromophore group.

11. The method of claim 1, wherein the tracer comprises at least one UV-VIS absorbing chromophore.

12. The method of claim 1, wherein the tracer comprises dye.

13. The method of claim 1, wherein the tracer comprises a component comprising one of a charge, isotope mass, or radioactive activity.

14. A method to control a fluid chemical composition, comprising:
   introducing an inert tracer in a component;
   forming a fluid comprising the component that contains the tracer;
   determining a concentration of the tracer in the fluid online;
   estimating a concentration of the component in the fluid based on the online determination of the concentration of the tracer in the fluid;
   adjusting an addition rate of the component during the forming in response to the estimating; and
   introducing the fluid into a subterranean formation.

15. The method of claim 14, wherein the estimating further comprises comparing the estimated concentration to a target concentration.

16. The method of claim 14, wherein the adjusting the addition rate of the component comprises sending a signal to a pump, screw feeder, shaker feeder and/or control valve.

17. The method of claim 14, wherein the adjusting the addition rate of the component comprises changing a flow rate of the component.

18. The method of claim 14, further comprising introducing a second tracer in a second component and wherein the fluid further comprises the second component.

19. The method of claim 14, wherein the tracer comprises organic molecules that can be quantified by liquid or gas chromatography.

20. The method of claim 14, wherein the tracer comprises organic molecules that can be detected by chromatography detectors.

21. The method of claim 14, wherein the tracer comprises organic molecules that can be detected by UV or visible spectroscopy.

* * * * *